Nov. 25, 1947. L. J. MARMON Plant Pat. 767
CARNATION PLANT
Filed March 26, 1947
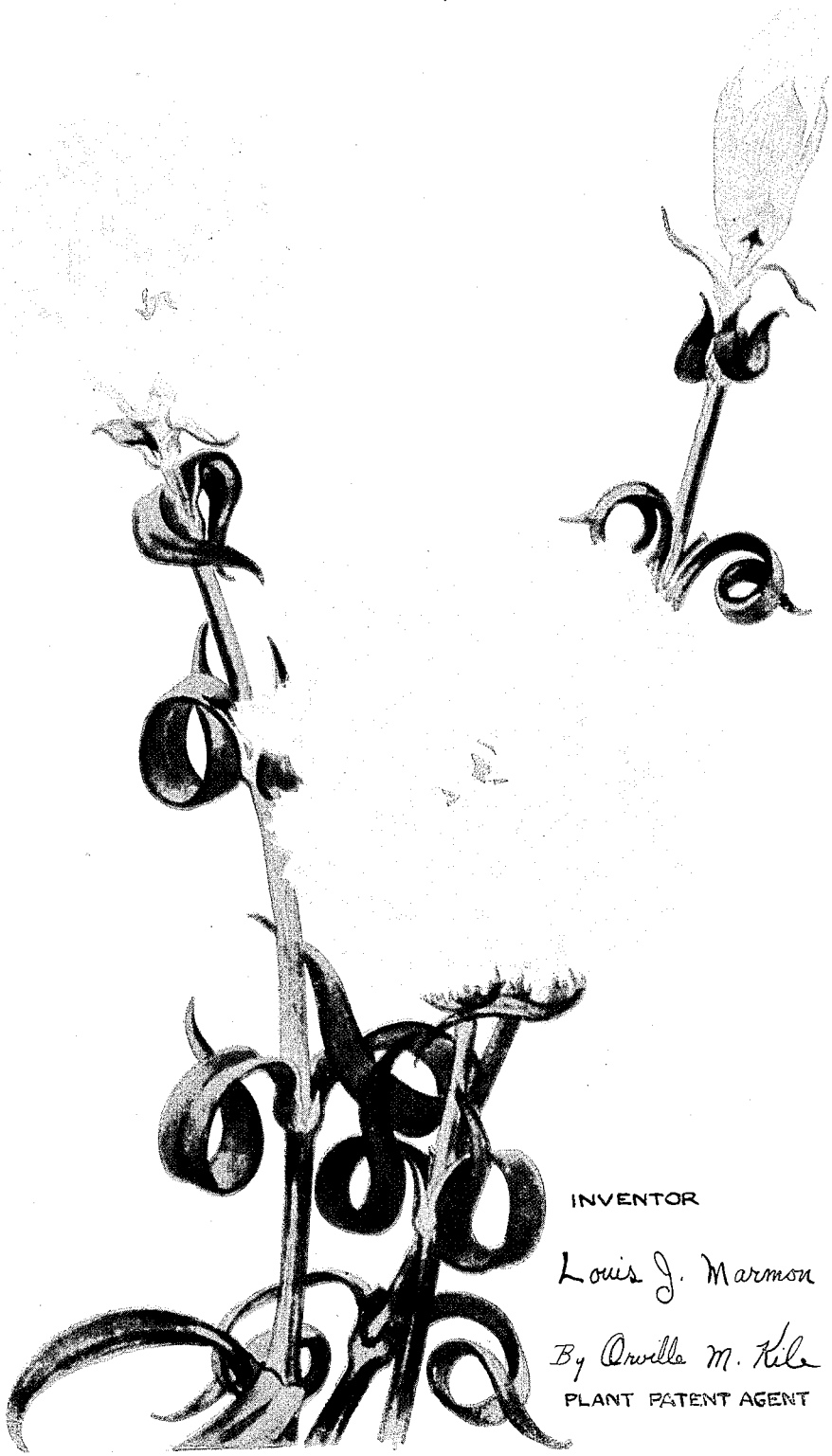
INVENTOR
Louis J. Marmon
By Orville M. Kile
PLANT PATENT AGENT Patented Nov. 25, 1947

Plant Pat. 767

UNITED STATES PATENT OFFICE

767

CARNATION PLANT

Louis J. Marmon, Springfield, N. J., assignor to
Louis J. Marmon Company, Springfield, N. J.

Application March 26, 1947, Serial No. 737,204

1 Claim. (Cl. 47—60)

My present discovery relates to an improved variety of greenhouse carnation plants and originated as a sport of the variety Patrician. It is a very prolific producer, enabling us to cut more flowers than from the parent variety. The plant is a strong grower and produces good strong flower stems. The flowers are full bodied and of a delicate pink color which is new on the market. Although the flower is large, its calyx does not split and the flower keeps longer in water than any other of the thousands of carnations of various varieties grown at our greenhouses.

This new variety has been asexually reproduced through several generations and its characteristics appear to be firmly fixed.

Accompanying illustrations show three specimens of the new variety in various stages of opening, in approximately their true colors and somewhat enlarged in the original paintings.

Following is a detailed description of this new variety. Color references indicate Ridgway's Color Standards and Nomenclature.

*The plant*

Growth: Strong, vigorous grower; very healthy. Branches freely, producing a somewhat grassy growth with a goodly number of cuttings.

Productivity: Excellent producer of good flowers, considerably surpassing its parent in this respect.

Reproduction: Many side shoots are formed and these root very readily.

Stems:

*Strength.*—Very strong, holding heavy flower perfectly erect.

*Color.*—Same as foliage except at nodes.

*Internodes.*—First pair of leaves embraces calyx, second pair only about ½ inch below. Other internodes medium length.

Foliage:

*Quantity.*—Considerable because internodes are relatively short and the foliage itself is medium to large.

*Size.*—Medium to large in both width and length, measuring up to $\frac{7}{16}$ inch in width and 4½ inches in length.

*Color.*—Approximately Civette Green (Plate XVIII) with slight gray bloom. This is rather light for carnation foliage and goes well with the delicate pink color of the flower.

*Nature.*—Curling.

*The flower*

Bud:

*Color.*—When beginning to open, the color is between Rose Pink (Plate XII) and La France Pink (Plate I).

*Size.*—Large. Just as it begins to break, it averages 1¼ inches long by ¾ inch wide.

*Shape.*—Broad but not blunt.

*Calyx.*—Broad and tough, seldom splitting. Color is approximately Biscay Green (Plate VI) at bottom. Consists of single tube with five lobes.

Bloom:

*Size.*—Large, measuring 3½ inches in diameter when grown under good conditions.

*Petalage.*—45 to 50.

*Form.*—Symmetrical, even, high-centered, full-bodied.

*Fragrance.*—Delicate cinnamon fragrance.

*Color.*—Approximately a true Cameo Pink (Plate XXVI), uniformly spread over the entire flower. This is a new shade in pink carnations and is very delicate, although it is retained well throughout the life of the bloom.

*Petals.*—Medium in weight. Outer petals 1¼ inches wide, 2½ inches long. Edges only slightly serrated.

*Longevity.*—As a cut flower in water, the keeping qualities are better than of any other of the many carnations grown by us. It also lasts well on the plant.

Reproductive organs:

*Stamens.*—Few; white; topped with small dull yellow anthers.

*Pistils.*—Usually two, arising from top of ovary; white; short, approximately 1 inch in length.

*Ovary.*—Unusually small compared to the large size of the flower.

*Comparison*

The known carnation variety which is most like my new variety is its parent, Patrician. The principal differences between the two varieties are as follows:

1. The flowers of the two varieties are of different color—my new one being a delicate tint of pink, while Patrician is white with an occasional pink streak.

2. The flower of my new variety is more symmetrical and fuller bodied.

3. The flower of my variety does not split its calyx, while the flower of Patrician has a tendency to split.

4. The flower of my new variety keeps much longer as a cut flower in water.

5. My variety produces a considerably greater number of flowers per plant during a season, and they are of consistently good quality.

6. The stems of my new variety are stronger and heavier.

7. The internodes of the stems of my new variety are shorter, bringing the foliage closer together.

Having thus disclosed my discovery, I claim:

The new and improved variety of carnation plant substantially as herein shown and described, characterized particularly by its healthy and vigorous growth; its ease of propagation; its strong stems with relatively short internodes; its prolific production of good, full bodied flowers which do not split; the cameo pink color of its flowers; and the unusual longevity of the flowers, particularly when cut and placed in water.

LOUIS J. MARMON.